United States Patent [19]
Jordan

[11] Patent Number: 4,630,038
[45] Date of Patent: Dec. 16, 1986

[54] VAPOR CONCENTRATION CONTROL

[76] Inventor: Mark A. Jordan, 9802 Tiverton Way, Louisville, Ky. 40222

[21] Appl. No.: 605,875

[22] Filed: May 1, 1984

[51] Int. Cl.$^4$ ............................................. G08B 17/10
[52] U.S. Cl. ..................................... 340/632; 73/1 G; 73/23
[58] Field of Search .................. 340/632, 633; 73/1 G, 73/23

[56] References Cited

U.S. PATENT DOCUMENTS

| | | | |
|---|---|---|---|
| 3,801,972 | 4/1974 | Ho Kim et al. | 340/633 X |
| 4,209,300 | 6/1980 | Thibault | 73/1 G X |
| 4,390,869 | 6/1983 | Christen et al. | 340/632 |
| 4,531,398 | 7/1985 | Di Benedetto et al. | 73/1 G |

Primary Examiner—Charles A. Ruehl
Assistant Examiner—Daniel Myer
Attorney, Agent, or Firm—Edward M. Steutermann

[57] ABSTRACT

A method and device for continuously analyzing, retaining and periodically displaying the concentration of a selected component in an emission gas from a vapor recovery unit. A timing device is provided to periodically display the average concentration of the component in the off gas and the concentration is continuously monitored and supplied to first and second level alarms to be actuated at selected concentrations of the component where when the concentration reaches the first level the concentration is displayed and where if the concentration reaches the second level the vapor recovery unit may be shut down.

6 Claims, 2 Drawing Figures

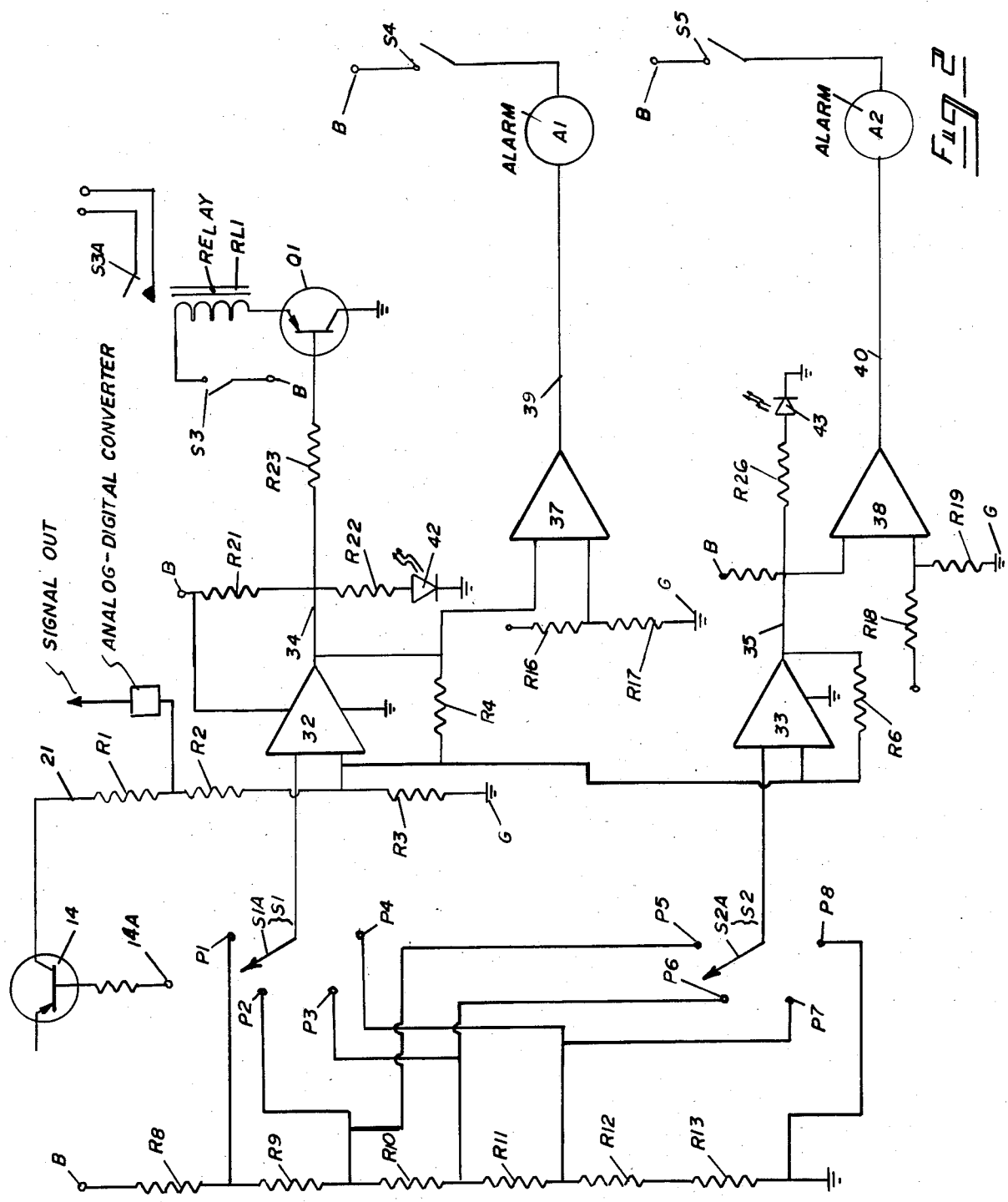

VAPOR CONCENTRATION CONTROL

SUMMARY OF THE INVENTION

The present invention provides a new and useful arrangement for monitoring the concentration of a selected component, for example hydrocarbon content in an off gas stream. For example in filling tanks such as petroleum storage tanks or gas tank trucks the air which is displaced by the petroleum products is satuated with the petroleum vapor.

The vapor concentration usually exceeds minimum clean air standards and emissions of the vapor to the atmosphere would constitute an air pollution control violation. Equally as important is the fact that the petroleum vapor has value and is economically worth recovery. In many instances solvent recovery systems are provided where the vapor in the off gas is recovered for example by refrigeration or absorption. In prior art arrangements the off gas has been periodically sampled for hydrocarbon concentration and the data recorded for compliance with environmental regulations.

No prior art device is known which provides means for continuously monitoring the off gas from a solvent recovery unit and provide first and second level alarms to indicate when the hydrocarbon concentration is out of a selected range. Further, no prior art device is known which provides the means to display the concentration of the hydrocarbon at selected intervals where the figure displayed is an average value over a selected time period to provide a more accurate indication of the effectiveness of the recovery unit where if the concentration of the hydrocarbon is increased above a first selected minimum on an instantaneous basis an alarm is actuated and if the concentration exceeds a second minimum the recovery unit can be shut down.

BACKGROUND OF THE INVENTION

The present invention provides method and apparatus to continuously monitor the concentration of a component in the exhaust hydrocarbon a vapor recovery system. Monitoring is provided to prevent excess loss of, for example hydrocarbons into the atmosphere to both reduce product loss and to notify equipment operators of a potential system failure or system deterioration which could lead to operating difficulty, safety hazards and possible pollution control violation.

In accordance with the present invention the vent gas from the solvent recovery unit is continuously monitoring and analyzed by a nondispersive analyzer. The concentration of hydrocarbon in the exhaust gas is then converted to an electrical signal which provides input signals to a two level alarm device and to a recording and display device. The recording and display device is time actuated to periodically store the instantaneous concentration of the selected component at selected intervals and then display an average overall concentration for the selected period of time as a permanent record.

The two level alarm system is adapted to actuate the display device at a first selected concentration of the component in the vent gas to inform the operating personnel of possible system deterioration or system failure and further to provide a permanent record of the hydrocarbon concentration at the time. Additionally a second level alarm is provided when the concentration of the component in the vapor has recorded a second limit to shut down the vapor recovery equipment, for example in the event of a total failure of the system.

More particularly, the present invention provides a method and device for continuously analyzing, retaining and periodically displaying the concentration of a selected component in an emission gas from a vapor recovery unit. A timing device is provided to periodically display the average concentration of the component in the off gas and the concentration is continuously monitored and supplied to first and second level alarms to be actuated at selected concentrations of the component where when the concentration reaches the first level the concentration is displayed and where if the concentration reaches the second level the vapor recovery unit may be shut down.

While various arrangements within the scope of the present invention will occur to those skilled in the art upon reading the disclosure set forth hereinafter, one example in accordance with the present invention is illustrated in the accompanying figures where it will be understood the accompanying figures and the description are not by way of limitation.

BRIEF DESCRIPTION OF THE DRAWINGS

In an arrangement in accordance with the present invention is shown in the Figures:

FIG. 2 is a schematic diagram of an alarm circuit useful in devices within the scope of the present invention.

DETAILED DESCRIPTION OF THE DRAWINGS

Figure 1:
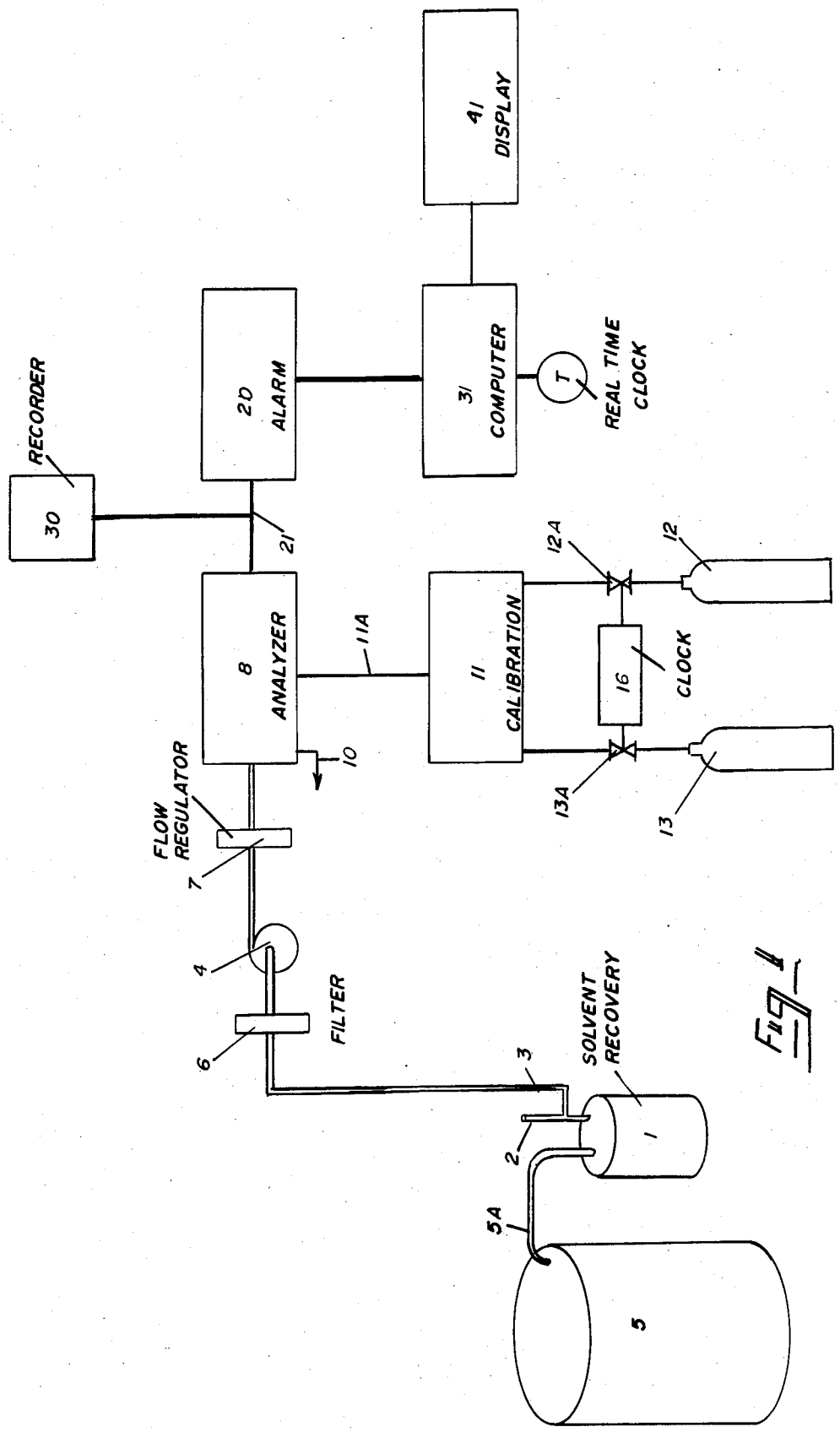
FIG. 1, is a schematic diagram of the operation of a system within the scope of the present.

FIG. 1 presents an illustration of an arrangement within the scope of the present invention including a tank 5 where off gas from the tank is supplied by means of a conduit 5A to a solvent recovery device 1 as shown. Solvent recovery device 1 can for example, be a refrigeration device or a carbon adsorption unit all as is known in the art to remove selected components, such as hydrocarbons from the air exhausted from tank 5 when, for example, the tank is filled with liquid such as petroleum product or other hydrocarbon liquid. Such arrangements are typically found in chemical processing plants, petroleum unloading facilities or the like.

Air is emitted from the solvent recovery device through an outlet 2 where a sample outlet conduit 3 is provided to a pump 4 which continuously draws a sample of gas through a filter 6 which is located between the vent 2 and the pump 4. A flow regulator 7, as known in the art, is provided on the outlet of pump 4 to assure constant rate of flow of gas.

The continuous flow of outlet gas is supplied to an analyzer 8, in this case a nondispersive infra-red analyzer, for example a model VIA nondispersive infra-red analyzer manufactured by Horiba Instruments, Inc.

Analyzer 8 can be adapted to measure the concentrations of several gasses and can measure wide concentration ranges of the gases including carbon monoxide, carbon dioxide, sulfur compounds, nitrogen compounds, methane, propane, or other hydrocarbons such as octane or those commonly encountered in industrial or chemical processes. The gas stream of selected flow volume is emitted from analyzer 8 by means of an exhaust outlet 10 upon completion of the analytical procedure.

Further within the scope of the present invention a calibration device 11 can be provided to be supplied with a standard mixture of gases from a source 12 through a valve 12A which can be a solenoid valve and timed as to be periodically opened to admit the standard gas mixture to the calibration device to set the calibration of the analyzer. For example the standard gas mixture would include known concentrations of the gases to be analyzed so that when the calibration device is actuated the output signal 11A from the calibration device sets the signal level of the analyzer, to calibrate the upper end of the range. A second gas source 13 such as nitrogen can be provided to supply a base line to be utilized to calibrate the lower end of the analyzer 11. The automatic calibration device follows a time schedule, for example by a time clock 16 illustrated schematicly to automatically correct the output signal and meter display of the infra-red analyzer by supplying pure nitrogen for a zero reading and a gas mixture of selected concentration for the span reading. An override 14 can be provided to an alarm system discribed hereinafter to prevent alarm during a period when the calibration is occurring.

An output signal 21 is provided from the infra red analyzer, which in this case can be a 0–1Vdc signal indicative of the concentration of hydrocarbon in the gas sample withdrawn from vent 2. The 0–1Vdc signal is supplied to an alarm system 20 described in more detail with reference to FIG. 2. The input signal 21 is also supplied as signal 25 to a computer 31 which receives the signal on a continuous basis. Computer 31 includes a real time clock T, which is programmed to periodically record the data reflecting concentration in memory. After a selected period of time, for example 5 minute or 10 minute interval, the time clock then actuates the computer to average the data points received during the time interval and display the data on a display device 41, for example a printer or a simple cathode ray tube display.

Signal 21 can also be supplied to a continuous display device such as a strip chart recorder 30 for continuous monitoring.

Referring now to FIG. 2, the input signal 21 is supplied through resistors R1 and R2 in series to one input of a comparator 32. The signal is grounded at G through a resistor R3 and is also supplied to one input of a second comparator 33 before the resistor R3.

As shown a feedback loop is provided through resistor R4 for comparator 32 and through resistor R6 for comparator 33. The outputs 34 and 35 of comparator 32, 33 are supplied respectively to Op amps 37, 38 with their other inputs supplied with reference voltage Vcc as selectively modified by resistors R16–R19 as shown to appropriately adjust the operating characteristic of amps 32, 33. Outputs 39, 40 from amplifiers 37, 38 are provided to alarm devices A1 and A2 in series with the outputs 39 and 40. Switches S4 and S5 are supplied in series with alarms A1 and A2 to provide a manual "turn off" for the alarms.

In the case of signal 34 supplied from comparator 32 the signal is also supplied through a base resistor R23 to a transistor Q1 having its emitter grounded and its collector connected through a relay coil RL1 to a relay switch S3A which is connected then to switch S3. Relay R1 closes switch S3A for automatic shut down of the vapor recovery unit in the event the concentration of the selected component reaches a selected level indicative of system failure.

Comparators 32 and 33 can be selectively adjusted to be actuated at selected concentrations by means of the second inputs to the comparators 32, 33 which are supplied reference signals through stepper switches S1 and S2 from a reference voltage B which is supplied through a resistor ladder R8, R9, R10, R11, R12 and R13 to ground where the poles P1–P4 of switch S1 provide the selected voltage reference to be supplied to the first inputs of comparators 32, and the poles P5–P8 of switch S2 provide the reference voltage to comparator 33 at different concentration levels by proper selection of the position of contacts S1A and S2A a range of alarm concentrations can be selected. Thus the device can be adjusted so that comparator 32 is actuated at a given component concentration and shuts down unit 1 which at a voltage corresponding to a position of contact S2A on contacts P5–P8 the comparator 33 is actuated to actuate alarm A2.

As previously described, means can be provided to "turn off" the alarm system when analyzer 8 is in calibration. In this regard, a NPN transistor 14 is supplied in series in output 21 from analyzer 8 and the base is connected to output 14A from timer 16 so that when timer 16 is actuated no signal is supplied to the alarm circuit shown in FIG. 2.

It will be understood that the forgoing is but one arrangement within the scope of the present invention and that various other arrangements within the scope of the present invention will occur to those skilled in the art upon reading the disclosure setforth hereinbefore.

The invention claimed is:

1. An arrangement for monitoring the concentration of a selected component in a gas stream including:
   (a) a source of said selected component which supplies a stream of gas containing said selected component;
   (b) sampling means to continuously receive a sample of said gas stream;
   (c) analyzer means to receive said gas stream and analyze said gas stream to determine the concentration of said selected component and provide a first electrical signal proportional to the concentration of said component in said gas stream;
   (d) reference signal generator means adapted to generate second reference electrical and third reference electrical signals including adjust means to selectively adjust the value of said second and third reference electrical signals;
   (e) first comparator means to receive said first electrical signal and said second reference electrical signal and provide a first comparator output signal to actuate a first alarm if said first electrical signal exceeds said second reference electrical signal, and second comparator means to compare said first electrical signal with said third reference electrical signal and provide second comparator output signal to actuate a second alarm if said first electrical signal exceeds said third reference electrical signal.

2. The invention of claim 1 including data memory means and data recorder means including real time clock means where said first electrical signal is continuously supplied to said data memory means and said real time clock and said memory means causes said recorder means to record an integrated value indicative of the average said first electrical signal at selected time intervals.

3. The invention of claim 2 wherein said memory means is adapted to receive at least one of said first and second comparator output signals and cause said recorder means to record a value indicative of said first electrical signal upon receipt of at least one of said first and second comparator signals.

4. An arrangement for monitoring the concentration of a selected component in a gas stream including:
   (a) a source of said selected component which supplies a stream of gas containing said selected component;
   (b) sampling means to continuously receive a sample of said gas stream;
   (c) analyzer means to receive said gas stream and analyze said gas stream to determine the concentration of said selected component and provide a first electrical signal proportional to the concentration of said component in said gas stream;
   (d) reference signal generator means adapted to generate second reference electrical and third reference electrical signal including adjust means to selectively adjust the value of said second and third reference electrical signals;
   (e) first comparator means to receive said first electrical signal and said second reference electrical signal and provide a first comparator output signal to actuate a first alarm if said first electrical signal exceeds said second reference electrical signal, and second comparator means to compare said first electrical signal with said third reference electrical signal and provide second comparator output signal to actuate a second alarm if said first electrical signal exceeds said third reference electrical signal;
   (f) data memory means and data recorder means including real time clock means where said first electrical signal is continuously supplied to said data memory means and said real time clock and said memory means causes said recorder means to record an integrated value indicative of the average said first electrical signal at selected time intervals wherein said memory means is adapted to receive at least one of said first and second comparator output signals and cause said recorder means to record a value indicative of said first electrical signal upon receipt of at least one of said first and second comparator signals.

5. The invention of claim 4 including gas analyzer means having real clock means to periodically supply gas streams of known concentration of said selected component to said analyzer means whereby the calibration of said analyzer means is reset in accordance therewith.

6. The invention of claim 4 including flow termination means to terminate flow of said gas stream in response to one of said first and second comparator signals.

* * * * *